(12) United States Patent
Gusek et al.

(10) Patent No.: US 11,623,967 B2
(45) Date of Patent: *Apr. 11, 2023

(54) PROCESS FOR OBTAINING CITRUS FIBER FROM CITRUS PULP

(71) Applicant: Cargill, Incorporated, Wayzata, MN (US)

(72) Inventors: Todd Walter Gusek, Crystal, MN (US); Jacques Andre Christian Mazoyer, Carentan (FR); David Hiram Reeder, Chanhassen, MN (US); Joel Rene Pierre Wallecan, Vilvoorde (BE)

(73) Assignee: Cargill, Incorporated, Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/882,481

(22) Filed: Jan. 29, 2018

(65) Prior Publication Data

US 2018/0155454 A1  Jun. 7, 2018

Related U.S. Application Data

(62) Division of application No. 13/812,603, filed as application No. PCT/US2011/045975 on Jul. 29, 2011, now abandoned.

(Continued)

(30) Foreign Application Priority Data

Jul. 30, 2010 (EP) .................................... 10008317

(51) Int. Cl.
C08B 37/00 (2006.01)
A23L 33/22 (2016.01)
(Continued)

(52) U.S. Cl.
CPC ............ C08B 37/0003 (2013.01); *A23L 2/52* (2013.01); *A23L 19/07* (2016.08); *A23L 29/206* (2016.08);
(Continued)

(58) Field of Classification Search
CPC ...... C08B 37/0003; A23L 33/22; A23L 19/07; A23L 29/206; A23L 2/52; A23K 10/37;
(Continued)

(56) References Cited

U.S. PATENT DOCUMENTS 3,658,790 A * 4/1972 Bernardin ................. C08B 5/00
536/34
4,497,836 A 2/1985 Marquardt et al.
(Continued)

FOREIGN PATENT DOCUMENTS

CN 1078111 A 11/1993
CN 101297687 A 11/2008
(Continued)

OTHER PUBLICATIONS

"Method for producing water-soluble dietary fiber", Machine Translation, CN101297687A, Nov. 5, 2006.
(Continued)

*Primary Examiner* — Subbalakshmi Prakash

(57) ABSTRACT

A process is disclosed for obtaining citrus fiber from citrus pulp. Citrus fiber is obtained having a c* close packing concentration value of less than 3.8. The citrus fiber can be obtained having a viscosity of at least 1000 mPa.s, wherein said citrus fiber is dispersed in standardized water at a mixing speed of from 800 rpm to 1000 rpm, to a 3 w/w% citrus fiber/standardized water solution, and wherein said viscosity is measured at a shear rate of 5 s-1 at 20° C. Citrus fiber can be obtained having a CIELAB L* value of at least 90. The citrus fiber can be used in food products, feed
(Continued)

products, beverages, personal care products, pharmaceutical products or detergent products.

20 Claims, 2 Drawing Sheets

Related U.S. Application Data

(60) Provisional application No. 61/369,204, filed on Jul. 30, 2010.

(51) Int. Cl.
| | |
|---|---|
| A23L 19/00 | (2016.01) |
| A23L 29/206 | (2016.01) |
| C11D 3/382 | (2006.01) |
| A61Q 19/00 | (2006.01) |
| A61K 36/752 | (2006.01) |
| A61K 8/97 | (2017.01) |
| A23L 2/52 | (2006.01) |
| A61K 8/9789 | (2017.01) |
| C08L 99/00 | (2006.01) |
| C08H 8/00 | (2010.01) |
| C08L 97/02 | (2006.01) |
| C08H 99/00 | (2010.01) |
| A23K 10/37 | (2016.01) |
| A23K 20/163 | (2016.01) |

(52) U.S. Cl.
CPC ............... *A23L 33/22* (2016.08); *A61K 8/97* (2013.01); *A61K 8/9789* (2017.08); *A61K 36/752* (2013.01); *A61Q 19/00* (2013.01); *C08H 8/00* (2013.01); *C08H 99/00* (2013.01); *C08L 97/02* (2013.01); *C08L 99/00* (2013.01); *C11D 3/382* (2013.01); *A23K 10/37* (2016.05); *A23K 20/163* (2016.05); *A23V 2002/00* (2013.01); *A61K 2800/10* (2013.01); *A61K 2800/48* (2013.01); *Y02P 60/87* (2015.11)

(58) Field of Classification Search
CPC ...... C11D 3/382; A61Q 19/00; A61K 36/752; A61K 8/97; Y02P 60/877; A23V 2250/636; A23V 2002/00
USPC ........................................................ 426/616
See application file for complete search history.

(56) References Cited

U.S. PATENT DOCUMENTS

| | | | |
|---|---|---|---|
| 5,213,836 A | 5/1993 | McGillivray | |
| 5,976,603 A | 11/1999 | Yang et al. | |
| 6,183,806 B1 | 2/2001 | Grossman et al. | |
| 6,183,906 B1 | 2/2001 | Shimozono | |
| 2002/0127312 A1 | 9/2002 | McArdle et al. | |
| 2004/0086626 A1* | 5/2004 | Lundberg | A23L 33/24 426/658 |
| 2005/0074542 A1 | 4/2005 | Lundberg et al. | |
| 2006/0115564 A1 | 6/2006 | Passarelli et al. | |
| 2009/0260768 A1 | 10/2009 | Kim | |
| 2010/0233342 A1 | 9/2010 | Almeida Rivera et al. | |
| 2013/0123374 A1 | 5/2013 | Gusek et al. | |
| 2013/0131012 A1 | 5/2013 | Gusek et al. | |
| 2014/0356463 A1 | 12/2014 | Gusek | |
| 2018/0009749 A1 | 1/2018 | Qin et al. | |
| 2018/0153199 A1 | 6/2018 | Reeder | |
| 2018/0155454 A1 | 6/2018 | Reeder | |
| 2018/0155869 A1 | 6/2018 | Reeder | |

FOREIGN PATENT DOCUMENTS

| | | | |
|---|---|---|---|
| CN | 101797037 A | 8/2010 | |
| CN | 101014252 B | 3/2011 | |
| CN | 103002755 | 3/2013 | |
| CN | 101863955 B | 3/2015 | |
| EP | 0295865 B1 | 1/1994 | |
| EP | 0495030 B1 | 11/1994 | |
| EP | 0485030 B1 | 9/1995 | |
| MX | 339585 | 6/2016 | |
| WO | WO-9427451 A1 * | 12/1994 | ............... A23L 2/62 |
| WO | WO 9733688 | 9/1997 | |
| WO | WO-2006033697 A1 * | 3/2006 | ............... A21D 2/36 |
| WO | 2008062057 A1 | 5/2008 | |
| WO | 2009075851 A1 | 6/2009 | |
| WO | 2010060778 A1 | 6/2010 | |
| WO | 2011131457 A1 | 10/2011 | |
| WO | 2011131457 W | 10/2011 | |
| WO | 2012016190 A1 | 2/2012 | |
| WO | 2012016201 A2 | 2/2012 | |
| WO | 2013109721 A2 | 7/2013 | |
| WO | 2017019752 W | 2/2017 | |

OTHER PUBLICATIONS

Chau, Chi-Fai , et al., "In Vitro Hypoglycemic Effects of Different Insoluble Fiber-Rich Fractions Prepared from the Peel of Citrus Sinensis L. cv. Liucheng", J. Agric Food Chem. 51(22), Oct. 22, 2003, 6623-6626.
Dong-Lin, Su , et al., "The Advance in Investigation of Functional Compounds in Citrus Peels and Their Extraction", Machine Translation, Modern Food Science and Technology, vol. 23 No. 3, Mar. 15, 2007, 90-94.
"Herbacel AQ Plus Citrusfaser", (Mar. 21, 2002), Lot. Nr. 3202036.
"Herbacel AQ Plus Citrus-N07", Citrusfaser feines hellgelbes pulver, (Jul. 6, 2011),p. 1, XP055598538.
"Microwave Release of Pectin for Orange Peel Albedo Using a Close Vessel Reactor System", Luzio, G. Proc. Fla State Hort, Soc, 121:315-319, 2008.
"Processed and Derived Products of Oranges" by CM Lanza. Encyclopedia of Food and Sciences Nutrition (2003) pp. 1346-1354.
"Production of water-soluble orange peel fiber", Database WPI, 0, Derwent World Patents Index, vol. 2010, No. 62, Database accession No. 2010-L27774, XP002710484 & CN 101797037 A Aug. 11, 2010 (Shaoyang College) [X] 1,9,10,16-18 abstract A 11-15 I 2-8.
Abandonment notice dated Apr. 4, 2018 and Non-Final Office Action dated Sep. 8, 2017 regarding Amended Claims of U.S. Appl. No. 13/812,623 of Aug. 10, 2017.
Abstract band Dietan' Fibre—2000, Dublin, Ireland, accompanying document for proving the publication date of FIscher 2000 Poster.
Amended claims of U.S. Appl. No. 13/812,623 of Aug. 10, 2017.
Anton Paar Instruction Manual MCR series, Feb. 2016.
AOAC's reply to Cargill's inquiry.
Carpita Nicholas C, Gibeaut David M, "Structural models of primary cell walls inflowering plants. Consistency of molecular structure with the physical properties of thewalls during growth", The Plant Journal, (Jan. 1, 1993), vol. 3, No. 1, pp. 1-30,XP055828122.
Chapter 2.4 (passage), Abraham Aserin, Multiple Emulsions—technology and applications.
Citrofiber DF-50 Classification download from http/www.faqs.org/rulings/rulings1991NY0860474.html on Apr. 19, 2019 (Mar. 22, 1991).
Claudia Pickardt et al., "the influence of mechanical and enzymaticdisintegration of carrots on the structure and properties of cell wall materials", Eur FoodRes Technol, (2004), vol. 219, pp. 229-239, XP055598547.
Complete Chapter II of of D27 already in proceedings.
Curriculum Vitae of Prof. Dr. Stephan Drusch.
Declaration of Dr. Joel Wallecan.
Deleris, I. et al., "Relationship between processing history and functionalityrecovery after rehydration of dried cellulose-based suspensions—A critical review", Adv.Coll. Interface Sci., (2017), vol. 246, doi—10.1016/j.cis.2017.06.013, XP085142725.
Delivery Documents for "Herbacel AQ plus Citrus" from Nov. 2009.
Dietary Fiber, Dublin 2000—Conference Announcement.

(56) References Cited

OTHER PUBLICATIONS

Diniz J. M.B., Et Al, "Hornification—its origin and interpretation in wood pulps", Woodsci Technol, (Jan. 1, 2004), vol. 37, pp. 489-494, XP055828118.
Dongowski, G. et al., "Binding of water, oil, and bile acids to dietary fibers of thecellar type", Biotechnol. Prog., (1999), vol. 15, doi—10.1021/bp990014c, pp. 250-258, XP055053455.
Dr. Wallecan's CV.
Excerpt from the textbook "Rheologie Handbuch", Thomas G. Mezger, Vincentz Network, Hannover, Germany, 2008, pp. 208-210.
Experimental Data.
Expert Opinion of Prof. Dr. Stephan Drusch.
Eyholzer et al., "Preparation and characterization of water-redispersiblenanofibrillated cellulose in fiber form", Cellulose, (2009), vol. 17, pp. 1-30,XP019767584.
Ferguson, R.R. et al., "Dietary Citrus Fibers", ASME 1978 Citrus Engineering Conference (CEC1978), USA, (1987), pp. 23-33, XP055597612.
Fischer 2000 Poster "Functional Properties of Herbacel AQ Plus Fruit Fibers" for Dietary Fibre 2000, Dublin, Ireland.
Fischer, J., "Functional Properties of Herbacel AQ Plus Fruit Fibers", (May 13, 2000), XP008137836.
Herbafood "Fruit and More", Flussiges Obst, pp. 1-6 (May 2002).
CC's reply to Cargill's Inquiry.
Kato K L, Cameron R E, "A review of the relationship between thermally acceleratedageing of paper and hornification", Cellulose, (Jan. 1, 1999), vol. 6, pp. 23-40,XP055828121.
Kunzek et al., "Einsatz der Druckhomogenisierung zur Herstellung vonzellstrukturiertem Apfelmaterial", Zeitschrift für Lebensmittel-Untersuchung und -Forschung, (1994), vol. 198, pp. 239-243, XP055597603.
Kunzek Herbert, Et Al., "The significance of chemical properties of plant cell wallmaterials for the development of innovative food products", Eur. Food Res. Technol.,Springer Verlag, (Mar. 28, 2002), vol. 214, pp. 361-376, XP055828091.
Kunzek, "Hydratationseigenschaften von Zellwandmaterialien und Ballaststoffen",Deutsche Lebensmittel-Rundschau, (2005), vol. 101, No. 6, pp. 238-255,XP055597600.
Lab Report 156/17.
Laboratory report 086/20, generated by the R&D department of Herbstreith & Fox, Mar. 3, 2020.
Laboratory report regarding the influence of different measuring geometries on the viscosity measurement.
Lewicki Piotr P, "Effect of pre-drying treatment, drying and rehydration on plant tissueproperties—A review", Int. Journal of Food Properties, (Jan. 1, 1998), vol. 1, pp. 1-22,XP055828102.

M. M. Farid, Mathematical Modeling of Food Processing, Taylor & Francis Group,(Jan. 1, 2010), p. 53, ISBN 978-1-4200-5351-7, XP055762492.
Mcconell, A.A. et al., "Physical characteristics of vegetable foodstuffs that couldinfluence bowel function", J Sci. Food Agric., (1974), vol. 25, pp. 1457-1464,XP055828094.
Mohammed M. Farid, Mathematical Modeling of Food Processing, (2010), p. 53, XP055763403.
Müller et al., "Material properties of processed fruit and vegetables", Zeitschrift fürLebensmittel-Untersuchung und -Forschung, (1998), vol. 206,doi—10.1007/s002170050255, pp. 264-272, XP055298035.
Nr. 156/17—ohne LA—Teilbericht, Labor-bericht, (Nov. 10, 2018), pp. 1-9, XP055598544.
Original Article Fischer, J. Flussiges Obst 2002, 5: 319-321.
Product Specification of the Herbacel AQ Plus Citrusfaser, lot No. 3202046, Mar. 21, 2002.
Prothon, F. et al., "Mechanisms and prevention of plant tissue collapse duringdehydration—a critical review", Crit Rev. Food Sci. Nutr., (2010), vol. 43, pp. 447-379, XP055828099.
Renard C M, Thibault J-F, "Composition and Physico-chemical Properties of AppleFibres from Fresh Fruits and Industrial Products", Lebensmittel-Wissenschaft und -Tecnologie, (Jan. 1, 1991), vol. 24, pp. 522-527, XP055828113.
Reply to Written Opinion prepared by the EPO for EP 3372093 A1, submitted by Cargill dated Feb. 27, 2019.
Scientific Report (Apr. 15, 2019).
Steenecken, P.A.M., Carbohydrate Polymers, 11, 23, 1989.
Submission in Proceedings EP 11741728.7 (Oct. 22, 2013).
Submission in proceedings EP 2597968 B1 (Oct. 22, 2013).
Supercritical CO2—A Green Solvent.
Table of Contents of Journal "Flussiges Obst", May 2002.
Test Report NR. 156/17 Vom Nov. 10, 2018.
The Influence of Mechanical and Enzymatic Disintegration of Carrots on the Structure and Properties of Cell Wall Materials, Claudia Pickardt, Gerhard Dongowski and Herbert Kunzek, Eur Food Res Technol (2004).
Thimm, J.C. et al., "Celery (*Apium graveolens* L.) parenchyma cell walls examined byatomic force microscopy—effect of dehydration on cellulose microfibrils", Planta,(2000), vol. 212, pp. 25-32, XP055828097.
Thomas G Mezger, Rheologie Handbuch. Excerpt, Hannover, Germany, VincentzNetwork, (Jan. 1, 2008), pp. 208-210, XP055762488.
Title Page of Journal Flussiges Obst, May 2002.
Vandeputte et al., J. Ceral. Sci., 38, 53, 2003, Rice starches. II. Structural aspects provide insight into swelling and pasting properties.
Written Opinion of the ISA to WO2012/016201A2.

\* cited by examiner

PROCESS FOR OBTAINING CITRUS FIBER FROM CITRUS PULP

CROSS-REFERENCE TO RELATED APPLICATIONS

This application is a Divisional of U.S. patent application, Ser. No. 13/812,603, filed Jan. 28, 2013, and entitled PROCESS FOR OBTAINING CITRUS FIBER FROM CITRUS PULP, which claims the benefit of PCT Patent Application, Serial No. PCT/US11/045975, filed Jul. 29, 2011, entitled PROCESS FOR OBTAINING CITRUS FIBER FROM CITRUS PULP, which claims the benefit of Provisional Patent Application Serial No. 61/369,204 filed Jul. 30, 2010, entitled PROCESS FOR OBTAINING CITRUS FIBER FROM CITRUS PULP, which applications are hereby incorporated by reference herein in their entirety.

TECHNICAL FIELD

The present invention is directed to a process for obtaining citrus fiber from citrus pulp. The resulting dried citrus fiber is useful as a food additive in food products, feed products and beverages. The citrus fiber is also useful in personal care, pharmaceutical or detergent products.

BACKGROUND OF THE INVENTION

The prior art describes methods for extracting citrus fiber from citrus pulp.

For example, U.S. Pat. No 7,094,317 (Fiberstar, Inc.) describes a process for refining cellulosic material from organic fiber plant mass (such as citrus fruit). The process discloses a first step of soaking the organic fiber plant mass in an aqueous solution, draining the organic fiber plant mass and allowing it to sit for sufficiently long time to enable cells in the organic fiber plant mass to open cells and expand the organic fiber plant mass. The soaking step requires at least 4 hours and is reported to be critical to get the materials to fully soften. The soaked raw material is then refined under high shear and dried.

W.O. Patent Application No 94/27451 (The Procter & Gamble Company) describes a process for producing a citrus pulp fiber, wherein first an aqueous slurry of citrus pulp is prepared which is then heated to a temperature of 70° C. to 180° C. for at least 2 minutes. The slurry is then subjected to a high shear treatment.

W.O. Patent Application No 2006/033697 (Cargill, Inc.) describes a process of extracting citrus fiber from citrus vesicles. The process includes washing citrus vesicles with water, contacting the water washed vesicles with an organic solvent to obtain organic solvent washed vesicles, desolventizing the organic solvent washed vesicles and recovering dried citrus fiber therefrom.

While the prior art reports that citrus fiber with useful properties is obtained, there remains a need to further improve the characteristics of citrus fiber.

Hence, it is an object of the present invention to develop a process for obtaining citrus fiber from citrus pulp having improved properties versus the citrus fiber of the prior art. It is further an object of the present invention to obtain a citrus fiber which has good hydration ability and viscosifying properties.

SUMMARY OF THE INVENTION

The present invention, according to one aspect, is directed to a process for obtaining citrus fiber from citrus pulp. In one embodiment, citrus pulp is treated to obtain homogenized citrus pulp. The process further comprises a step of washing the homogenized citrus pulp with an organic solvent to obtain organic solvent washed citrus pulp. The organic solvent washed citrus pulp is desolventized and dried, and citrus fiber is recovered.

In another aspect the present invention is directed to a citrus fiber having a c* close packing concentration value of less than 3.8.

In a preferred embodiment, the citrus fiber has a viscosity of at least 1000 mPa·s, wherein said citrus fiber is dispersed in standardized water at a mixing speed of from 800 rpm to 1000 rpm, preferably 900 rpm, to a 3 w/w % citrus fiber/standardized water solution, and wherein said viscosity is measured at a shear rate of $5\ s^{-1}$ at 20° C. In another preferred embodiment, the citrus fiber has a CIELAB L* value of at least 90.

In yet another aspect, the present invention is directed to a blend of citrus fiber of the present invention and plant-derived (e.g. derived from cereals) fiber, citrus fiber obtained from citrus peel or citrus rag (segment membranes, core) and combinations thereof.

In yet another aspect, the present invention is directed to a food product, a feed product, a beverage, a personal care product, pharmaceutical product or a detergent product comprising the citrus fiber according to the present invention.

In yet another aspect, the present invention is directed to the use of the citrus fiber as a texturiser or viscosifier in food products, feed products, beverages, personal care product, pharmaceutical product or detergent product.

DETAILED DESCRIPTION OF THE INVENTION

Figure 1:
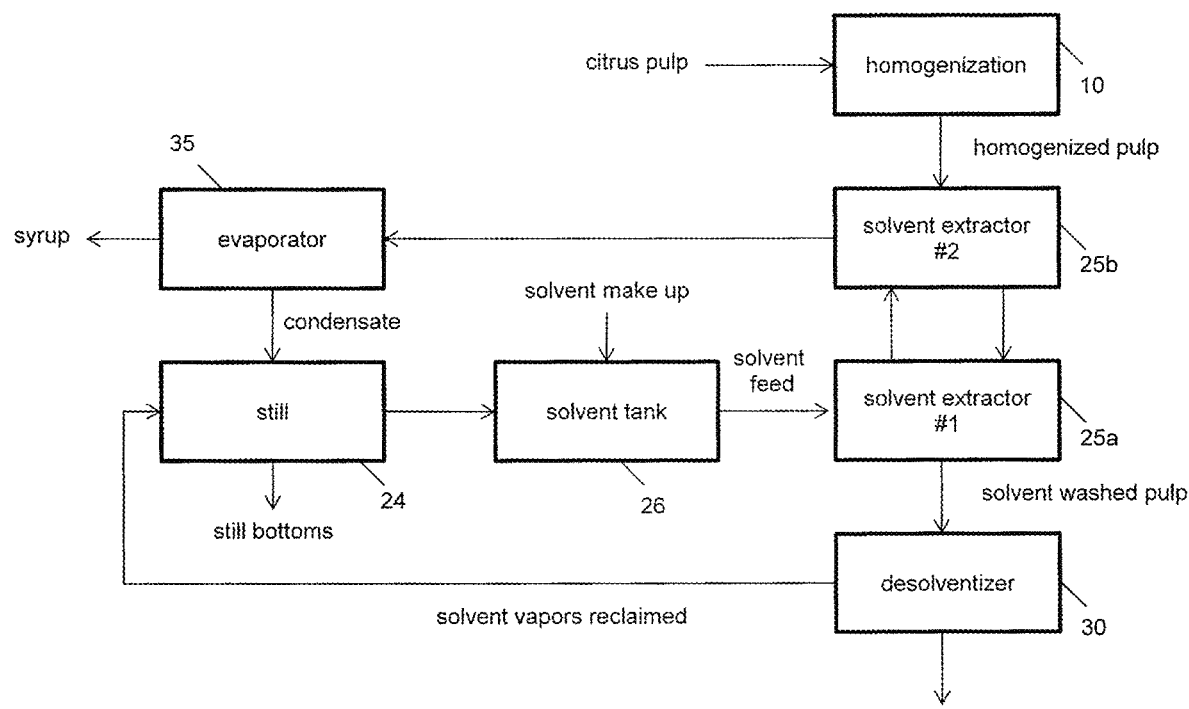
FIG. 1 is a schematic illustration of a process in accordance with a preferred embodiment of the present invention.

In one aspect, the present invention is directed to a process for obtaining citrus fiber from citrus pulp.

The term "citrus pulp," as used herein, refers to the pectinaceous and cellulosic material contained in the inner, juice-containing portion of citrus fruit. It is a co-product of the orange juice industry, resulting from the mechanical extraction of the juice. Citrus pulp is sometimes also referred to as coarse pulp, floaters, citrus cells, floating pulp, juice sacs, citrus vesicles or pulp. Citrus pulp typically has a water content of at least about 80 wt % and usually from about 90 to about 98 wt %.

The term "citrus fiber," as used herein, refers to a fibrous pecto-cellulosic component obtained from citrus pulp.

The process according to the present invention may be used for obtaining citrus fiber from citrus pulp from a wide variety of citrus fruit, non-limiting examples of which include oranges, tangerines, limes, lemons, and grapefruit. In one preferred embodiment, citrus fiber is obtained from orange pulp.

In the process according to the present invention, citrus pulp is treated to obtain homogenized citrus pulp. Optionally, the citrus pulp may be washed with water prior to homogenization. Sometimes, citrus pulp may be provided in a frozen or dried state which requires thawing or rehydration prior to homogenization. Preferably, the citrus pulp is adjusted with water to a dry matter content of 5 wt % or less. While not intending to be bound to any theory, it is believed that the homogenization treatment causes disruption and disintegration of whole pulp cells and cell fragments. Homogenization can be effected by a number of possible methods including, but not limited thereto, high shear treatment, pressure homogenization, colloidal milling, intensive blending, extrusion, ultrasonic treatment, and combinations thereof. Preferably, the power input (power per unit volume) for effecting homogenization is at least 1000 kW per $cm^3$ of citrus pulp.

In a preferred embodiment of the present invention, the homogenization treatment is a pressure homogenization treatment. Pressure homogenizers typically comprise a reciprocating plunger or piston-type pump together with a homogenizing valve assembly affixed to the discharge end of the homogenizer. Suitable high pressure homogenizers include high pressure homogenizers manufactured by GEA Niro Soavi, of Parma (Italy), such as the NS Series, or the homogenizers of the Gaulin and Rannie series manufactured by APV Corporation of Everett, Mass. (US).

During the pressure homogenization, the citrus pulp is subjected to high shear rates as the result of cavitation and turbulence effects. These effects are created by the citrus pulp entering the homogenizing valve assembly from the pump section of the homogenizer at a high pressure (and low velocity). Suitable pressures for the process of the present invention are from 50 bar to 1000 bar.

Depending on the particular pressure selected for the pressure homogenization, and the flow rate of the citrus pulp through the homogenizer, the citrus pulp may be homogenized by one pass through the homogenizer. However, more than one pass of the citrus pulp may be required.

In one embodiment, the citrus pulp is homogenized by a single pass through the homogenizer. In a single pass homogenization, the pressure used is preferably from 300 bar to 1000 bar, more preferably from 400 bar to 800 bar, even more preferably from 500 bar to 750 bar.

In another preferred embodiment, the citrus pulp is homogenized by multiple passes through the homogenizer, preferably at least 2 passes, more preferably at least 3 passes through the homogenizer. In a multipass homogenization, the pressure used is typically lower compared to a single-pass homogenization and preferably from 100 bar to 600 bar, more preferably from 200 bar to 500 bar, even more preferably from 300 bar to 400 bar.

Optionally, the citrus pulp may be subjected to a heat treatment prior to homogenization. Preferably, the temperature used in the heat treatment can vary from 50° C. to 140° C. for a period of from 1 second to 3 minutes. The heat treatment may be used for pasteurization of the citrus pulp. For pasteurization, the heat treatment preferably employs a temperature of from 65° C. to 140° C., preferably from 80° C. to 100° C. for a period of from 2 seconds to 60 seconds, preferably from 20 seconds to 45 seconds. Pasteurization is preferred to inactivate pectinesterases for preventing cloud loss and to inactivate spoilage micro-organisms for enhancing storage stability.

The homogenized citrus pulp is then contacted with an organic solvent. In one aspect, the organic solvent extracts water, flavors, odors, colors and the like from the citrus pulp. The solvent should preferably be polar and water-miscible to better facilitate removal of the desired components. Available solvents may include lower alcohols such as methanol, ethanol, propanol, isopropanol, or butanol. Preferred solvents are ethanol, isopropanol, and combinations thereof. The solvent may be provided in aqueous solution. The concentration of solvent in the solvent solution most often ranges from about 70 wt % to about 100 wt %. In one embodiment, a 75 wt % aqueous ethanol solution is used as solvent. In a preferred embodiment, a 90 wt % aqueous ethanol solution is used as solvent. In general, solvents will remove water-soluble components at lower concentrations and oil-soluble components at higher concentrations. Optionally, a more non-polar co-solvent may be added to the aqueous alcohol to improve the recovery of oil-soluble components in the citrus pulp. Examples of such non-polar solvents include ethyl acetate, methyl ethyl ketone, acetone, hexane, methyl isobutyl ketone and toluene. The more non-polar solvents may be added at up to 20% of the solvent mixture. Many solvents, such as ethanol, have a lower heat of vaporization than that of water, and therefore require less energy to volatilize than would be needed to volatilize an equivalent mass of water. The solvent preferably is removed and reclaimed for reuse.

Preferably, the citrus pulp is contacted with organic solvent at a solids-to-solvent weight ratio of at least about 0.25:1, preferably at least about 0.5:1, and often at least about 0.75:1, from about 1:1 to about 5:1, or from about 1.5:1 to about 3:1, based on the wet weight of the solids. In one embodiment, the solids-to-solvent ratio is about 2:1.

Extraction can be accomplished using a single stage but preferably is performed using multi-stage extraction, e.g., a two-, three-, or four-staged extraction process, and preferably using countercurrent extraction. There is no particular upper limit contemplated on the number of extraction stages that may be used. FIG. 1 schematically illustrates a preferred embodiment in which a two-stage countercurrent extraction process employs first and second solvent extractors 25a and 25b, respectively.

After homogenization 10, homogenized citrus pulp is fed into the second extractor 25b. An aqueous ethanol solvent is fed from a solvent tank 26 into the first solvent extractor 25a. Spent solvent from the first solvent extractor 25a is fed into the second solvent extractor 25b, while the extracted citrus pulp from the second solvent extractor 25b are fed into the first solvent extractor 25a. Spent solvent from the second solvent extractor 25b may be fed into an evaporator 35 (optional) to separate solids (e.g., sugars, acids, colors, flavors, citrus oils, etc.) from the spent solvent, which can be condensed and returned to a still 24. Still bottoms (predominately water) are separated and removed.

After each extraction stage, liquid is preferably further removed. One suitable device is a decanter centrifuge. Alternatively, a sieve, a belt filter press or other device suitable for removing liquids, may be used.

Citrus pulp from the first solvent extractor 25a is fed to a desolventizer 30. The desolventizer 30 removes solvent and water from the solids remaining after extraction, enabling the solvent to be reclaimed for future use and also ensuring that the product is safe for milling and commercial use. The desolventizer 30 can employ indirect heat to remove significant amounts of solvent from the solid residue. Alternatively, direct heat can be provided for drying, e.g., by providing hot air from flash dryers or fluidized bed dryers. Direct steam may be employed, if desired, to remove any trace amounts of solvent remaining in the solids. Vapors from the desolventizer 30 preferably are recovered and fed to the still 24 to reclaim at least a portion of the solvent.

Retention time in each extraction step may vary over a wide range but can be about 5 minutes or less per extraction step. The temperature in the solvent extractor(s) depends on such factors as the type of solvent used but most often ranges from about 4° C. to about 85° C. at atmospheric pressure.

Temperatures can be appropriately increased or decreased for operation under super- or sub-atmospheric pressures. Optionally, techniques such as ultra-sound are used for enhancing efficiency of the extraction process. By maintaining a closed system, solvent losses during extraction, desolventizing, and distillation can be minimized. Preferably, at least about 70 wt % of the solvent is recovered and reused. A solvent make-up stream delivers fresh solvent into the solvent tank 26 to replenish any solvent that is not recovered.

In a preferred embodiment, the process according to the present invention further comprises a comminuting or pulverizing step prior to desolventizing and drying. Suitable methods include, but are not limited to, grinding, milling, crushing, high speed mixing, or impingement. Comminution or pulverization can be beneficial to disintegrate any clumps or aggregates that are left after the removal of liquid with the belt filter pressing step. This step furthermore facilitates the removal of solvent. While not wishing to be bound by theory, it is believed that comminution or pulverization further opens the fibers. As a result of this, the solvent is more uniformly distributed and easier to be removed in the subsequent desolventization and drying step. In yet another preferred embodiment, the comminuting or pulverizing step is used in combination with adding and dispersing water or a blend of water and an organic solvent (as described hereinbefore) to enhance desolventization and drying, and achieve the desired humidity in the finally obtained citrus fiber for a particular end use.

In another preferred embodiment, the process according to the present invention further comprises a comminuting or pulverizing step after drying. This post-drying comminuting or pulverizing step may be carried out to further reduce the particle size of the citrus fiber, to improve flowability, dispersability, and/or hydration properties.

In yet another preferred embodiment, the process according to the present invention further comprises the step of subjecting the citrus pulp to a processing aid. Preferably, the processing aid is selected from the group consisting of enzymes, acids, bases, hydrocolloids, vegetable fiber, bleaching agent, and combinations thereof. Preferably, the processing aid is mixed with the citrus pulp prior to homogenization.

In one aspect of the present invention, the processing aid may be used to tailor the properties of the finally obtained citrus fiber.

Preferred enzymes include, but are not limited thereto, pectinase, protease, cellulase, hemicellulase and mixtures thereof. When enzymes are used, they are to be used prior to any heat treatment that would inactivate them, and preferably also prior to homogenization. Inactivation by heat treatment is however desired once the desired effect is achieved.

Preferred acids include, but are not limited thereto, citric acid, nitric acid, oxalic acid, ethylenediaminetetraacetic acid and combinations thereof. Citric acid is however most preferred as it is a food grade acid.

A preferred base is caustic soda.

Preferred hydrocolloids include, but are not limited thereto, pectin, alginate, locust bean gum, xanthan gum, guar gum, carboxymethylcellulose and combinations thereof.

A bleaching agent may further enhance the color properties (i.e. render the citrus fiber even more whiter). A preferred bleaching agent is hydrogen peroxide.

The citrus fiber obtained by the process according to the present invention has improved properties over other citrus fibers from the prior art. Especially, the citrus fiber has good swelling behavior, hydration ability and viscosifying properties. It is capable of building viscosity under relatively low shear.

The citrus fiber of the present invention has a c* close packing concentration of less than 3.8 w %, anhydrous basis. Preferably, the c* close packing concentration is less than 3.6, even more preferably less than 3.4, and most preferably less than 3.2 w %, anhydrous basis. The determination of the c* close packing concentration is described in the test method section herein below.

The citrus fiber preferably has a moisture content of 5% to 15%, more preferably from 6% to 14%. Preferably, at least 90% of the volume of the particles have a diameter of less than 1000 micrometers, preferably from 50 micrometers to 1000 micrometers, more preferably from 50 micrometers to 500 micrometers, even more preferably from 50 micrometers to 250 micrometers.

The citrus fiber preferably has a viscosity of at least 1000 mPa·s, wherein said citrus fiber is dispersed in standardized water at a mixing speed of from 800 rpm to 1000 rpm, preferably 900 rpm, to a 3 w/w % citrus fiber/standardized water solution, and wherein said viscosity is measured at a shear rate of 5 $s^{-1}$ at 20° C. Preferably, the viscosity at a shear rate of 5 $s^{-1}$ at 20° C. is at least 2000 mPa·s, more preferably at least 3000 mPa·s, even more preferably at least 4000 mPa·s, even more preferably at least 5000 mPa·s and up to 15000 mPa·s. The preparation of the standardized water, and the method for measuring viscosity is described in the test method section herein below.

The citrus fiber according to the present invention further has good emulsification properties, as shown in the examples. The D4,3 value in the oil-rich phase is typically below 15 micrometers for the citrus fiber of the present invention.

In a preferred embodiment, the citrus fiber of the present invention also has excellent whiteness properties, even without the need for using bleaching agents. The citrus fiber typically has a CIELAB L* value of at least 85. But with the process according to the present invention, it is possible to obtain much higher L* values. Thus, according to another aspect, the present invention is directed to a citrus fiber having a CIELAB L* of at least 90, preferably at least 92, even more preferably at least 93. Preferably, the citrus fiber has a CIELAB b* value of less than 20, even more preferably of less than 15. The method for determining the CIELAB L* and b* values is described in the test method section herein below. As discussed hereinbefore, bleaching agents may still be used as processing aids in the process to even further improve the whiteness of the citrus fiber.

The citrus fiber according to the present invention can be blended with other fibers, such as plant-derived (e.g. from vegetables, grains/cereals) fibers, with other citrus fibers such as citrus fiber obtained from citrus peel or citrus rag, or combinations thereof. The blend can be in dry or liquid form.

In another aspect, the citrus fiber of the present invention and the blends described hereinbefore may be used in food applications, feed applications, beverages, personal care products, pharmaceutical products or detergent products. The amount of citrus fiber (or blend) to be used depends on the given application and the desired benefit to be obtained, and lies within the knowledge of a skilled person.

Food applications may include, but are not limited to, dairy products, frozen products, bakery products, fats and oils, fruit products, confectionary, meat products, soups, sauces and dressings. Dairy products include, but are not limited to yoghurt, fromage frais, quark, processed cheese, dairy desserts, mousses. Frozen products include, but are not limited to, ice cream, sorbet, water ice. Bakery products include, but are not limited to, cakes, sweet goods, pastry, patisserie, extruded snacks, fried snacks. Fats and oils include, but are not limited to, margarines, low fat spreads, cooking fats. Fruit products include, but are not limited to, fruit preparations, yoghurt fruit preparations, conserves, jams, jellies. Confectionary includes, but is not limited to, candy, chocolate spreads, nut-based spreads. Meat products include, but are not limited to, chilled or frozen processed meat and poultry, preserved meat products, fresh sausage, cured sausage and salami.

Beverages may include concentrates, gels, energy drinks, carbonated beverages, non-carbonated beverages, syrups. The beverage can be any medical syrup or any drinkable solution including iced tea, and fruit juices, vegetable based juices, lemonades, cordials, nut based drinks, cocoa based drinks, dairy products such as milk, whey, yogurts, buttermilk and drinks based on them. Beverage concentrate refers to a concentrate that is in liquid form.

Personal care products may include cosmetic formulations, hair care products such as shampoos, conditioners, creams, styling gels, personal washing compositions, suncreams and the like.

Detergent products may include hard surface cleaning products, fabric cleaning or conditioning products, and the like.

Test Methods

1. Preparation of Standardised Water

Dissolve 10.0 g NaCl (e.g. Merck 1.06404.1000, CAS [7647-14-5]) and 1.55 g $CaCl_2.2H_2O$ (e.g. Merck 1.02382.1000, CAS [10035-04-8]) in low conductivity water (e.g. milli-Q Ultrapure Millipore 18.2 MΩcm), and make up to 1 liter to prepare standardized water stock. Take a 100ml aliquot of the standardized water stock and make up to 1 liter with low conductivity water.

2. Measuring c* Close Packing Concentration 2.1 Principle

Citrus fiber samples (n≥10) are wetted with ethylene glycol, dispersed in standardised tap water, and subjected to the MCR301 controlled shear stress (CSS) oscillatory test. The citrus fiber dispersions are measured by 0.25w/w% increments in the range of 1.75-5.00 w/w %. The linear viscoelastic range (LVR) complex moduli G* is plotted against concentration. The close-packing concentration c* is determined via the two tangents crossover method on a linear scale.

2.2 Apparatus

Anton Paar MCR301 rheometer with coaxial cylinder configuration (TEZ150P-CF Peltier at 20° C.) with vane probe ST24-2D/2V/2V-3D, grooved measuring cup CC27/T200/SS/P and circulating cooling water bath set at 15° C. The equipment must be clean and dry, and the MCR301 units must be turned on 30 minutes before use. Checks should be made according to the instruction manual of the supplier (see instruction manual). The Circulator bath and pump should be at all times in use to avoid burning of the peltier unit. According to the manufacturer, the water bath must be filled with demineralised water containing maximum 30% of antifreeze (e.g. ethylene glycol).

RWD 20 Digital IKA stirrer and lower the paddle (4 bladed propeller 07 410 00)

600 ml Duran glass beaker (ø10 cm)

Laboratory balance having a precision of 0.01 g

Hard plastic soup spoon 2.3 Procedure

System Start-Up

Start up the circulator bath (filled with demineralised water+30% ethylene glycol (e.g. Merck 1.00949.1000, CAS [107-21-1])) and afterwards the rheometer according to the procedure explained in the instruction manual. Select the workbook and perform the initialisation procedure according to the instruction manual.

System Calibration

The standard calibration check procedure for the MCR301 is fully described in the instruction manual and should be performed according to the instruction manual. The MCR301 instruments must be ready (initiated and all parameters checked) before testing the citrus fiber dispersions. The ST24 measuring system CSR should be set to 1 and the CSS value (Pa/mNm) should be fixed with certified calibration Newtonian oil (e.g. Cannon N100, available from Cannon Instrument Company, State College, Pa. 16803, USA).

Sample Preparation

Place a 600 ml glass beaker on the laboratory balance, and zero the balance.

Weigh into the beaker the required grams (x) of citrus fiber, to the nearest 0.01 g, according to the moisture content (m) of the citrus fiber sample: $x=3c/[(100-m)/100]$, for any given concentration c in w/w % (samples starting at 1.75 w/w %, to 5.00 w/w % with 0.25w/w % increments). The moisture content m should be determined by infra-red moisture balance (Sartorius MA 30), as weight loss at 105° C. with automatic timing, typically 3-4g citrus fiber covering the entire bottom of the aluminium pan. The moisture content (m) of citrus fiber is in weight percent (w %).

Weigh into a second 600 mL beaker the required grams (w) of standardised tap water, to the nearest 0.1 g, according to the moisture of the citrus fiber sample: $w=270.0-x$ Place the beaker with CPF on the laboratory balance, zero the balance, add 30.0g (to the nearest 0.1 g) of ethylene glycol, put the beaker out of the balance and mix the content with the plastic spoon thereby wetting the whole powder (this operation is performed within 60 seconds).

Pour at once the standardised tap water on to the wet citrus fiber and mix the content with the plastic spoon by repeated clockwise and anti-clockwise rotations (this operation is performed within 60 seconds).

Position the glass beaker with its content (citrus fiber, ethylene glycol, standardised tap water) underneath a RWD 20 Digital IKA stirrer and lower the paddle (4 bladed propeller 07 410 00) into the paste until 2 cm from the bottom of the glass beaker.

Adjust the paddle speed (rpm) to 900 rpm and stir 10 minutes at 900 rpm.

Cover the beaker with aluminium foil and allow 24 hours rest prior measurement

Pour the required amount of CPF dispersion into the cylindrical cup of the rheometer and insert immediately the vane probe ST24 (starch cell probe) into the cylinder containing the CPF dispersion Sample Analysis Perform CSS oscillatory test with the MCR301 according to the manual instructions, with 2 segments:

segment 1: non recording, 10 minutes at 20° C. (equilibration)

segment 2: recording, 1971 seconds at 20° C., 50 measuring points integration time 100 to 10 seconds log, torque 1 to 10,000 µNm log, frequency 1 Hz Results At low stress, where the G* (versus stress) is showing constant plateau values, average the G* results over the linear viscoelastic range. Using the software "LVE Range", the end of the linear viscoelastic region in the CSS experiments can be determined.

Plot the LVR G* versus concentration. The first tangent at low concentration (below c*) has a much lower slope than the second tangent at high concentration (above c*). Using linear fitting (e.g. with Microsoft® Excel®), the crossover point of both tangents occurs at the close packing concentration c*.

3. Measuring Viscosity

Add citrus fiber to standardized water in a beaker with a paddle mixer to obtain a 3 wt % citrus fiber dispersion with a total volume of 300 ml. Prior to adding the citrus fiber, create a vortex by adjusting the paddle speed to 900 rpm using an IKA Overhead Mechanical Stirrer RW20 equipped with a 4-bladed propeller stirrer. Then add the citrus fiber quickly (before the viscosity builds up) on the walls of the vortex under stirring (900 rpm using an IKA Overhead Mechanical Stirrer RW20 equipped with a 4-bladed propeller stirrer). Continue stirring for 15 minutes at 900 rpm. Store the sample for 12 hours at 20° C.

Then perform the viscosity test with a rheometer (e.g. Anton Paar MCR300), in accordance with the rheometer's instructions, in function of shear rate (from 0.01 to 100 s$^{-1}$) at 20° C.

The viscosity (mPa·s) is determined at a shear rate of 5 s$^{-1}$.

4. Emulsification

Prepare an emulsion containing 20 wt % sunflower oil, 2 wt % citrus pulp fiber and the remaining standardized tap water. First disperse the fiber in the water phase under high-shear mixing (8000 rpm) for 1 minute. Then add the oil to the water phase under high-shear mixing (13500rpm) for 5 min at room temperature and constant mixing speed.

Figure 2A:
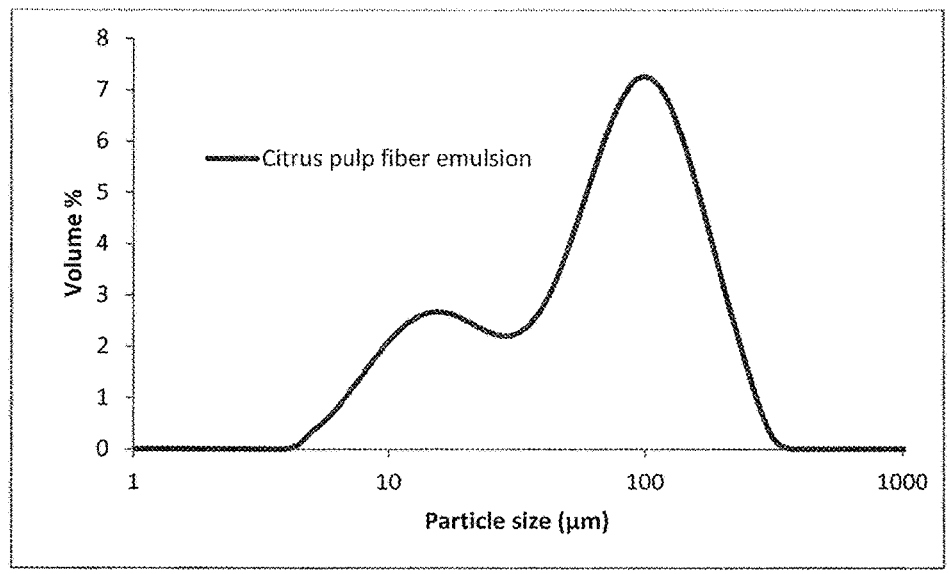
FIGS. 2*a* and 2*b* are an illustration in accordance with a test method used in the present application.

Particle size distribution of the obtained emulsions is measured using laser light scattering (e.g. using a Malvern MasterSizer X). Typically, a bimodal particle size distribution is observed (see FIG. 2a). The peak on the right corresponds with the particle size distribution of the oil-rich fraction of the emulsion (oil droplets+soluble fibers), while the peak on the left corresponds with the particle size distribution of the insolubles-rich fraction of the emulsion (e.g. cellulose).

The Malvern software allows the determination of an overall volume mean diameter D(4,3), but cannot provide the D(4,3) of the separate fractions. However, as fractions show a log-normal distribution, a peak deconvolution can be applied.

Peak deconvolution can be performed as follows: transfer the raw data from the Malvern MasterSizer X into Microsoft Excel™ for further analysis. It is assumed that the overall volume mean diameter (as obtained by the Malvern MicroSizer) equals the sum of 2 log-normal distributions.

Figure 2B:
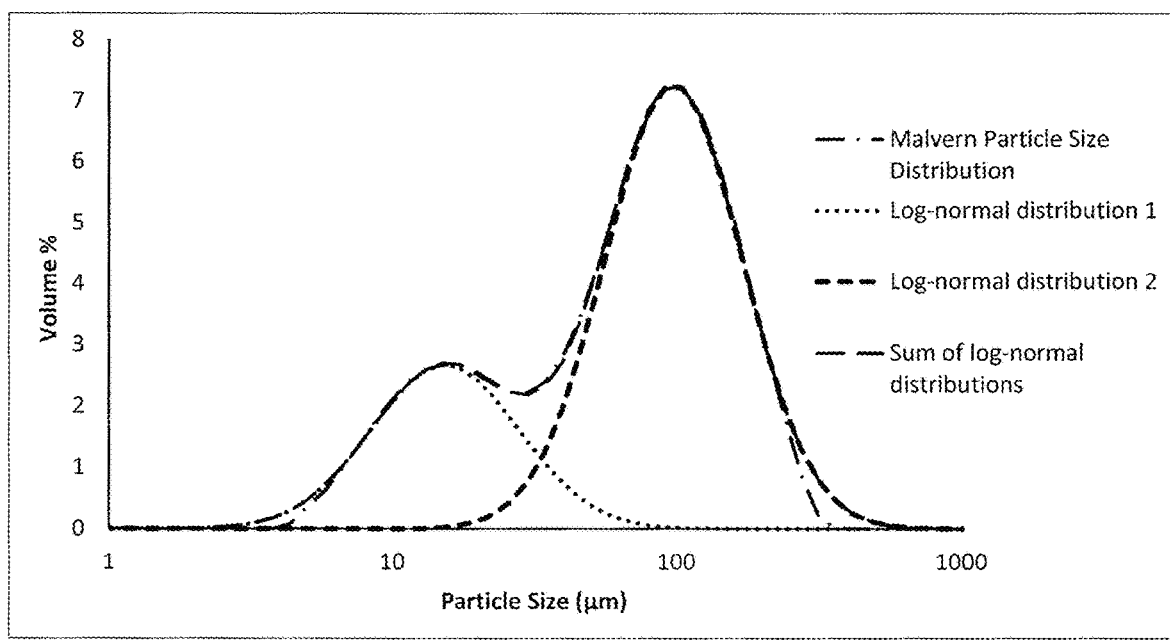

The equation for a log-normal distribution can be found in literature. The lognormal distribution is a two-parameter distribution with parameters µ' and σ$_T$. The probability density function for this distribution is given by:

$$f(T') = \frac{1}{\sigma_{T'}\sqrt{2\pi}} e^{-\frac{1}{2}\left(\frac{T'-\mu'}{\sigma_{T'}}\right)^2}$$

where T'=In(T), where the T values correspond with the particle sizes in the present method, and
µ'=mean of the distribution
σ$_T$=standard deviation of the distribution Deconvolution can be performed based on this equation and the results obtained are shown in FIG. 2b.

A good fit is found between the raw data distribution and the applied model. The mean (µ') of the peaks of each distribution corresponds with the D(4,3) of each phase (oil-rich phase and insolubles-rich phase). This assumption can be made due to the fact that the particles follow an almost perfect log-normal distribution.

5. Measuring Colour (CIELAB L*, b* Values)

CIE L*a*b* (CIELAB) is the most complete color space specified by the International Commission on Illumination (Commission Internationale d'Eclairage). It describes all the colors visible to the human eye and was created to serve as a device independent model to be used as a reference. The L* and b* values of the citrus fiber are obtained by placing citrus fiber (in powder form) in the glass cell (fill the cell to about a half) of the colorimeter and analyse the sample in accordance with the user's instructions of the colorimeter. The colorimeter used is a Minolta CR400 Colorimeter.

EXAMPLES

1. Examples 1-5

Orange pulp is adjusted with water to a dry matter content of 5 wt % to obtain 720 kg of the orange pulp. The pulp is charged to a pressure homogenizer (Niro Soavi, type NS3006L) and recirculated (maximum 5 bar) while adjusting the feed pressure to 700 bar.

The precipitation tank is filled with a centrifuge pump with 1.8 m$^3$ of 75-80 wt % ethanol solution from the first washing tank. The homogenized pulp is sent straight to the precipitation tank with a volumetric pump. Agitate while filling the tank, and continue stirring for about 30 minutes.

Adjust the speed of the centrifuge decanter (Flottweg centrifuge, 900R150, decanter Z23-3) to 5260 rpm. The differential speed is adjusted to 30 rpm and the diameter adjustment to 145 mm. Charge the product to the centrifuge decanter with a volumetric pump, and recover the product.

First ethanol washing: a tank is filled with 1.5 m$^3$ of 82 wt % ethanol solution from the second ethanol washing. Feed the recovered product into the tank, and agitate for about 30 minutes. The washed product is then sent to a 100 µm rotative filter with a volumetric pump, and product is recovered.

Second ethanol washing: send the recovered product from the first ethanol washing to a tank filled with 1.4 m$^3$ of 85 wt % ethanol solution, and agitate for about 30 minutes. The washed product is then sent to a 100 µm rotative filter with a volumetric pump, and product is recovered.

The recovered product from the second ethanol washing is then fed to a screw press. The speed and pressure is adjusted to obtain a dry matter content of about 30 wt %.

The product is then milled using a Lodigue, 900M340, type FM300DIZ, and mill for 15 to 30 minutes.

The product is then fed to a vacuum dryer (ECI) and mixed for about 90 minutes. Add slowly 40% (based on dry matter content of the product) of a 60% ethanol solution. Dry with 95° C. water for 4 hours under vacuum.

Recover the orange pulp fiber.

5 samples (Ex. 1-5) are prepared, originating from Brazilian orange pulp from different sources.

2. Comparative Example

The orange pulp fiber obtained by the process of the present invention is compared to commercially available citrus fibers:

Citri-Fi 100 and Citri-Fi 100 M 40, orange fiber derived from orange pulp (Fiberstar Inc.)

Herbacel AQ-Plus Citrus Fibre F/100, and Herbacel AQ-Plus Citrus Fibre N, lemon fibers derived from lemon peel (Herbstreith & Fox Inc).

3. Results

3.1 c* Close Packing Concentration

|  | c* (w %, anhydrous basis) |
|---|---|
| Example 4 | 2.80 |
| Example 5 | 3.09 |
| Citri-Fi 100 | 4.04 |
| Herbacel AQ-Plus Citrus Fibre N | 3.94 |

The c* close packing concentration of the citrus fiber according to the present invention is significantly lower than those of the commercially available fibers.

3.2 Viscosity

|  | viscosity (mPas) |
|---|---|
| Example 1 | 7085 |
| Example 2 | 4455 |
| Example 3 | 13000 |
| Example 4 | 6900 |
| Example 5 | 22890 |
| Citri-Fi 100 | 508 |
| Herbacel AQ-Plus Citrus Fibre F/100 | 250 |

A significant difference in viscosity is observed between the orange fibers according to the present invention (ex. 1-5), and the commercially available fibers.

Furthermore, an additional test has been carried out. It has been assessed at with mixing speed (versus the 900 rpm used in the test method), about the same level of viscosity increase could be obtained for a commercial citrus fiber. For the Citri-Fi 100 sample, a viscosity of 7545 mPa·s could be obtained if the citrus fiber is dispersed in the standardized water only at high shear rates (9500 rpm). This shows the benefit of the citrus fiber of the present invention in that it can build viscosity even when dispersed in solution at low shear rates. This means that the citrus fiber of the present invention is much easier to process and provides economical advantages (equipment and energy) over the fibers of the prior art.

3.3 Emulsification

|  | D4, 3 (μm) oil-rich phase | D4, 3 (μm) insolubles-rich phase |
|---|---|---|
| Example 1 | 7.7 | 74.0 |
| Example 5 | 9.2 | 77.5 |
| Citri-Fi 100 M 40 | 31.1 | 59.8 |
| Herbacel AQ-Plus Citrus Fibre F/100 | 18.1 | 113.9 |

It can be observed that the D4,3 value in the oil-rich phase is much lower for the orange fiber of the present invention (example 1, 5). This means that the oil droplets in this phase are much smaller and hence prove the better emulsification behavior of the orange fiber of the present invention.

3.4 Colour

|  | L* | b* |
|---|---|---|
| Example 1 | 93 | 12 |
| Citri-Fi 100 M 40 | 87 | 15.3 |
| Herbacel AQ-Plus Citrus Fibre F/100 | 88 | 11.7 |

The orange fiber of the present invention has an L* value above 90, and is whiter than the commercial fibers.

What is claimed is:

1. A process for preparing citrus fibers from citrus pulp, the process comprising:
   treating citrus pulp to obtain homogenized citrus pulp, wherein the treating comprises pressure homogenization;
   subjecting the homogenized pulp to a bleaching agent;
   washing the homogenized citrus pulp with an organic solvent to obtain organic solvent washed citrus pulp;
   feeding the organic solvent washed citrus pulp through a screw press at a speed and pressure to obtain a dry matter content of about 30 wt % or more;
   milling the screw pressed citrus pulp for at least 15 minutes;
   vacuum drying the milled citrus pulp for at least 90 minutes adding at least 40% (db) of a 60% solvent solution;
   vacuum drying the vacuum dried citrus pulp with water at a temperature of at least 95° C. for at least 4 hours to remove the solvent; and
   recovering citrus fibers from the citrus pulp, wherein the citrus fiber has a D4,3 value less than 15 micrometers, wherein the recovered citrus fibers have a moisture content in a range of from 5% to 15% and a c* close packing concentration of less than 3.8 w %, anhydrous basis.

2. The process according to claim 1, wherein the treating comprises pressure homogenization using a pressure of from 50 bar to 1000 bar.

3. The process according to claim 2, wherein said treating comprises a single-pass pressure homogenization using a pressure of from 300 bar to 1000 bar.

4. The process according to claim 2, wherein said treating comprises a multi-pass pressure homogenization comprising at least 2 passes, using a pressure of from 100 bar to 600 bar.

5. The process according to claim 1, wherein the citrus pulp is subjected to a heat treatment prior to the homogenization treatment at a temperature of from 50° C. to 140° C. for a period of 1 second to 3 minutes.

6. The process according to claim 1, wherein said process further comprises subjecting said citrus pulp to a processing aid selected from the group consisting of enzymes, acids, bases, hydrocolloids, vegetable fiber, and combinations thereof.

7. The process according to claim 1, wherein the bleaching agent comprises hydrogen peroxide.

8. The process according to claim 1, wherein the organic solvent is selected from the group consisting of methanol, ethanol, propanol, isopropanol, butanol, and combinations thereof.

9. The process according to claim 1, wherein the organic solvent comprises ethanol, isopropanol, or combinations thereof.

10. The process according to claim 9, wherein the organic solvent further comprises an organic non-polar co-solvent.

11. The process according to claim 10, wherein the non-polar co-solvent comprises up to 20 wt % of a mixture of a polar organic solvent and the non-polar organic solvent.

12. The process according to claim 10, wherein the organic non-polar co-solvent comprises ethyl acetate, methyl ethyl ketone, acetone, hexane, methyl isobutyl ketone, toluene, or a mixture thereof.

13. The process according to claim 2, wherein said treating is a multi-pass pressure homogenization comprising at least 3 passes, using a pressure of from 100 bar to 600 bar.

14. The process according to claim 1, wherein the organic solvent has a solids-to-solvent weight ratio of at least about 0.5:1.

15. The process according to claim 1, wherein the organic solvent has a solids-to-solvent weight ratio in a range of from about 1:1 to about 5:1.

16. The process according to claim 1, wherein the organic solvent has a solids-to-solvent weight ratio in a range of from about 1.5:1 to about 3:1.

17. The process according to claim 1 further comprising applying a processing aid to the citrus pulp.

18. The process according to claim 17, wherein the processing aid comprises an enzyme, an acid, a base, a hydrocolloid, a vegetable fiber, or a mixture thereof.

19. The process according to claim 17, wherein the processing aid is applied to the citrus pulp prior to homogenization of the citrus pulp.

20. The process according to claim 1, wherein the recovered citrus fiber has a diameter of less than 1000 micrometers.

* * * * *